US00PP10512P

United States Patent [19]

Lemon

[11] Patent Number: Plant 10,512

[45] Date of Patent: Jul. 21, 1998

[54] VARIETY OF GERANIUM PLANT NAMED 'MAUREEN'

[75] Inventor: David Lemon, Lompoc, Calif.

[73] Assignee: John Bodger & Sons Company, So. El Monte, Calif.

[21] Appl. No.: 724,678

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 8,192 3/1993 Holden ..... Plt./87.12

*Primary Examiner*—Howard J. Locker

*Attorney, Agent, or Firm*—Fulwider Patton Lee & Utecht, LLP

[57] ABSTRACT

The cultivar is characterized by its medium green foliage and two-toned orange and white flower. Its relatively strong growth habit, quick rooting time and continuous flowering provide for superb cuttings and also for quick recovery following wet weather conditions. The blooms exhibit good post-harvest quality.

1 Drawing Sheet

BACKGROUND OF THE NEW PLANT

The present invention comprises a new and distinct cultivar of *Pelargonium×hortorum* known by the varietal name Maureen (Oglevee No. 1149, Bodger No. 1GM 47-1). The new variety was discovered in a selective breeding program by David Lemon at Bodger Seeds, Ltd., Lompoc, Calif. The new variety is a selection from the crossing of Bodger No. 10 GM 156-1 with Bodger No. 9 GM 111 (unpatented).

The new cultivar was first asexually reproduced by cuttings at Oglevee Ltd., Connellsville, Pa., and has repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa. using full light, 60° Fahrenheit night temperature, 68° Fahrenheit day temperature, and grown in a soilless media of constant fertilizer 200–250 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Mar. 14, 1996 under full light and greenhouse, and colorings were taken indoors under 200–220 foot candles of fluorescent cool white light using the R.H.S. Colour Chart of The Royal Horticultural Society of London.

The plant

Classification:

*Botanical.*—*Pelargonium×hortorum.*

*Commercial.*—Floribunda Geranium Maureen.

Form: Semi-dwarf, uniform mound with some lateral growth.

*Height.*—16.0–17.0 cm from media surface.

*Growth.*—Free basal branching, lateral and procumbent habit.

*Strength.*—Free and early flowering; may be used as a landscaping plant or in a hanging basket.

Foliage: Stalked leaf attachment.

Leaves:

*Size.*—5.0–8.0 cm across.

*Shape.*—Reniform: cordate base.

*Margin.*—Crenate.

*Texture.*—Pubescent.

*Color.*—Top: Green group 136C. Bottom: Green group 137D. Zone: Green group 137A.

*Ribs and veins.*—Palmate venation: Color: Yellow/green group 145B.

Petioles:

*Color.* —Yellow Green group 145B.

Stem:

*Color.*—Yellow-Green group 145B.

*Internodes.*—2.5–3.0 cm in length.

The Bud (Umbel)

Shape: Upright; hemispherical cluster.

Size: 2.0–2.5 cm across.

Inflorescence

Blooming habit: Upright; continuous, very floriferous.

Borne: 6–12 cm above foliage, floret on pedicel, pedicel on peduncle.

Closed florets:

*Bud size.*—0.5–1.0 cm.

*Size.*—Fully open bloom: 8.0–9.0 cm.

Open florets:

*Form.*—Semi double; cupped 16 florets appearing per inflorescence.

*Color.*—Upper Surface Bi Color—Overall appearance orange with a white eye Outer edge: Red Group 40D presents a strong impression at the outer edge of the petal which them graduates to Red group 52 D which is a paler color of orange therefore presenting a bicolor effect with a white eye. Base: White.

*Bottom.*—Outer edge Red group 41C which gradually fades to a pure white although the tint of the petal color does not change so as to produce a overall color impression which remains the same.

*Petals.*—13–16.

*Size.*—3.5–4.5 cm.

*Texture and appearance.*—Two-tone orange with a white eye.

Petaloids:

*Quantity.*—4–6.

*Shape.*—Curled, ruffled.

*Color.*—Top Red group 40D. Bottom: Red group 41C.

Pedicel:

*Length.*—1.5–2.25 cm.

*Color.*—Yellow-green group 145B.

Peduncle:

*Length.*—14–16 cm.

*Color.* —Yellow-green group 145B.

Persistence:

*Disease resistance.*—Not known.

*Lasting quality.*—Unknown.

Reproductive organs

Anthers:

*Length.*—1 mm–1.5 mm.

Filaments:

*Length.*—6–8 mm.

*Color.*—White.

Pollen: Golden brown.

Pistils:

*Number.—One.*

*Length.*—6.0–8.0 mm.

*Stigma.*—Color: White; 5–6 parted.

*Style.*—2 mm in Length.

*Ovaries.'*Color: Green; pubescent; Length: 4 mm; superior.

Fruit: None.

General Characteristics

Maureen adds a new orange and white bi-coloroed flower to the current group of light pink, pink, salmon and red floribundas. Floribundas are a group of plants of similar diploid heritage which exhibit related characteristics such as spreading habit, basal-branching, small numerous double flowers and heat tolerance. The floribundas are intermediate in plant habit between a zonal Geranium and an ivy Geranium. A neat mound growth habit lends itself well in containers or ground plantings. This variety exhibits very good cutting production, similar to the Elizabeth U.S. Plant Pat. No. 8,192, which has a more orange-red appearance and does not have the white eye which is characteristic of the claimed cultivar variety. The variety produces many flower clusters which create a continuous flowering bouquet above medium green foliage.

I claim:

1. A new and distinct variety of Geranium plant, substantially as shown and described.

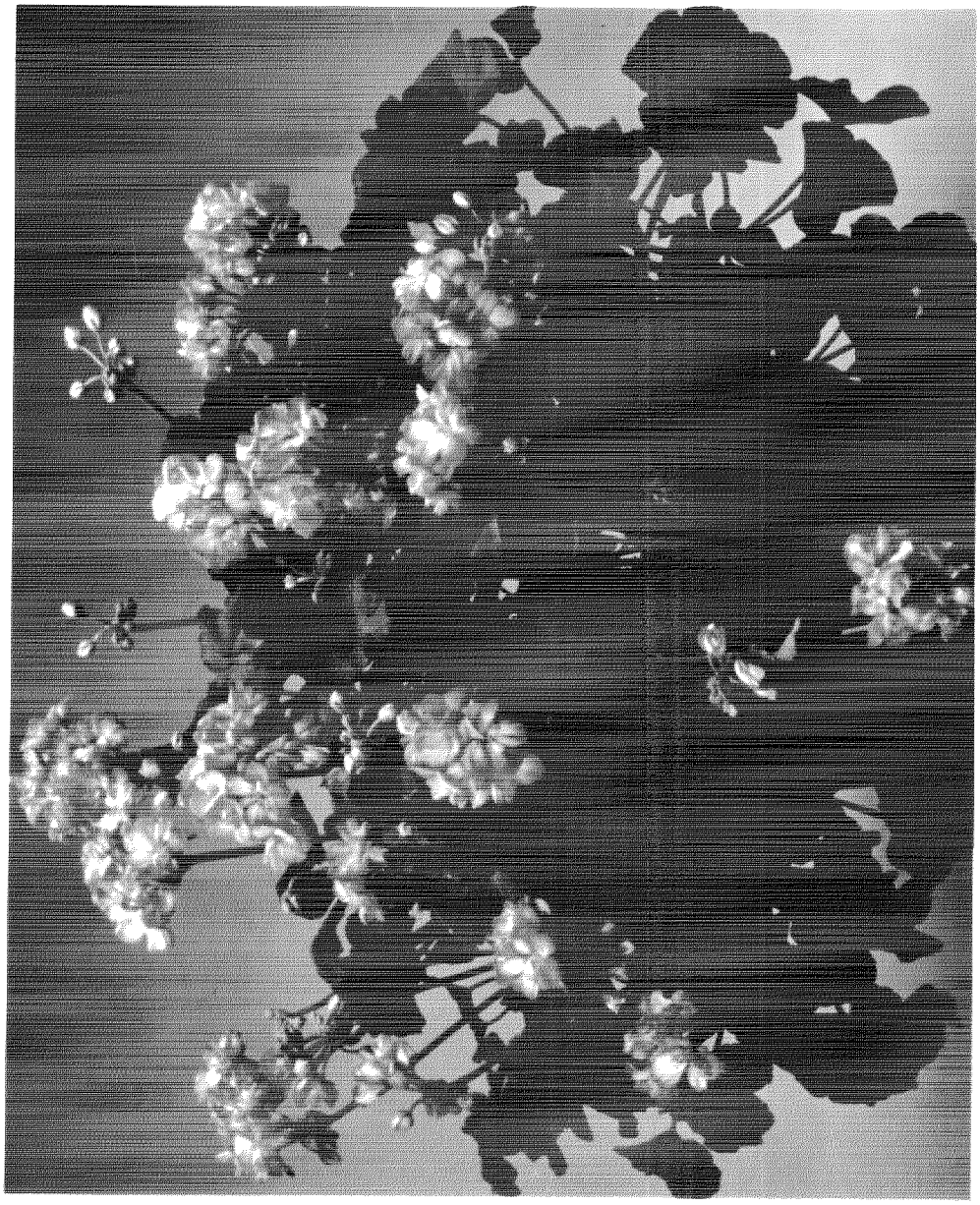

* * * * *